US007794584B2

(12) United States Patent
Chodavarapu et al.

(10) Patent No.: US 7,794,584 B2
(45) Date of Patent: Sep. 14, 2010

(54) PH-CHANGE SENSOR AND METHOD

(75) Inventors: Vamsy P. Chodavarapu, Verdun (CA);
Alexander N. Cartwright,
Williamsville, NY (US); Albert H. Titus, Buffalo, NY (US); Rachel M. Bukowski, Buffalo, NY (US); Frank V. Bright, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 1007 days.

(21) Appl. No.: 11/548,995

(22) Filed: Oct. 12, 2006

(65) Prior Publication Data

US 2007/0138028 A1 Jun. 21, 2007

Related U.S. Application Data

(60) Provisional application No. 60/725,777, filed on Oct. 12, 2005.

(51) Int. Cl.
*G01N 27/327* (2006.01)
*G01N 27/333* (2006.01)
*G01N 27/414* (2006.01)
(52) U.S. Cl. .................... 205/777.5; 257/253; 204/433; 204/403.01; 204/403.04; 205/787.5
(58) Field of Classification Search ................................
204/403.01–403.15, 416–418; 257/253
See application file for complete search history.

(56) References Cited

U.S. PATENT DOCUMENTS

| 4,882,292 | A | * | 11/1989 | Sudholter et al. ............. 438/49 |
| 5,309,085 | A | * | 5/1994 | Sohn .......................... 257/253 |
| 2002/0006632 | A1 | * | 1/2002 | Ponnampalam et al. .... 435/7.92 |
| 2004/0149577 | A1 | * | 8/2004 | Kumar et al. ........... 204/403.01 |

FOREIGN PATENT DOCUMENTS

EP 0080402 A1 * 11/1982

OTHER PUBLICATIONS

European Patent Office English language machine translation of the Description of Gautier et al. EP 0080402 A1, patent application published on Jun. 1, 1983.*
page 520 of Ng, Complete Guide to Semiconductor Devices, McGraw-Hill, Inc. 1995.*

* cited by examiner

*Primary Examiner*—Alex Noguerola
(74) *Attorney, Agent, or Firm*—Hodgson Russ LLP

(57) ABSTRACT pH-change sensors and related methods are disclosed. One such sensor may have a first ion-sensitive transistor-operational-transconductance-amplifier (the "first IOTA") and a second ion-sensitive transistor-operational-transconductance-amplifier (the "second IOTA"). Each IOTA may have an ion-sensitive transistor, a load transistor, and an output. In each IOTA, the drain region of the ion-sensitive transistor may be connected to the drain region of the load transistor. A differential sensor may be connected to the IOTAs, and an output from the differential sensor may indicate a voltage difference between the IOTA outputs. The output from the differential sensor may be used to provide an indication of a change in pH.

24 Claims, 9 Drawing Sheets

C: Active contact, C1: Poly contact, M1: metal 1 layer,
M2: metal 2 layer, Via: Metal 1 to Metal 2 connection P1, P2, P3 and P4 are p-MOSFETs and N1, N2, N3, N4 and N5 are n-MOSFETs.

PH-CHANGE SENSOR AND METHOD

CROSS-REFERENCE TO RELATED APPLICATION

This application claims the benefit of priority to U.S. provisional patent application Ser. No. 60/725,777, filed on Oct. 12, 2005.

GOVERNMENT FUNDING

This work was supported by funding from the National Science Foundation, Grant no. BES-0330240. The Government has certain rights in the invention.

FIELD OF THE INVENTION

The present invention relates to sensors and methods which detect changes in pH.

BACKGROUND OF THE INVENTION

There is a need for solid state sensors for use in many applications, including medicine, biotechnology, biomedical diagnosis, medical therapy and chemical analysis, as well as environmental and industrial monitoring. There is also a need for sensors that are small, light weight and which have a fast response. By integrating sensors with signal processing components in an integrated circuit (IC), very small sensors may be made. CMOS fabricating techniques have the advantage of offering potentially low cost devices that can be mass-produced. CMOS fabricating techniques also offer the potential for devices that require relatively less power to operate, are small, light weight, and fast. The present invention may use these techniques to provide a pH-change sensor.

The ion sensitive field-effect transistor (ISFET), as we know it today, was invented by Bergveld (Bergveld, IEEE Tran. Biomed. Eng., vol. 17, (1970), pp. 70-71), as a solid-state silicon-based chemical sensor. Since then, there has been significant research and development in extending the principle by integrating active recognition materials with ISFETs to form biologically-modified ISFETs (BioFETs), enzyme-modified ISFETs (EnFETs), immunologically-modified ISFETs (ImmunoFETs), DNA-Modified or gene-modified ISFETs (GenFETs) or chemically-modified ISFETs (ChemFETs). Each of the above-mentioned devices are selective to a specific analyte depending on the recognition material present on the ISFET. Most prior implementations of ISFETs with integrated recognition elements are discrete devices with specialized processing requirements that limit commercialization of the technology. In addition, the recognition materials or elements used in such devices may be suitable only for a particular analyte, thereby limiting the diversification of the sensors based on the same sensor platform. A detailed review of recent advances in such devices can be found in Schoning and Poghossian, Analyst, vol. 127, (2002), pp. 1137-1151.

A number of research groups have previously studied different methods of fabricating ISFETs using a modified standard CMOS process with additional process steps or using a standard CMOS process. Bousse et al., IEEE Electron Devices Letters, vol. 9, (1988), pp. 44-46, first proposed the combined fabrication of ion sensors and CMOS circuits on the same IC and more recently, Canè, et al., Sensors and Actuators, B, vol. 35-36, (1996) pp. 136-140 and Bausells, et al., Sensors and Actuators B, vol. 57, (1999), pp. 52-62, have used a multilayer gate structure for the ISFET for fabrication in a commercial CMOS processing technology.

In order to realize a pH-change sensor, an important component is the reference electrode, which provides the electrical contact to the test electrolyte and that provides a proper electrode-electrolyte potential irrespective of the composition of the electrolyte. In most of the previous implementations, the reference electrode was an Ag/AgCl electrode, and due to its size and complexity this electrode severely limited the applicability and the advantages of developing ISFETs in a CMOS process.

A practical solution to the above problem is to use a differential ISFET configuration with a noble metal electrode (either gold or platinum) as the pseudo or quasi reference electrode. Several implementations of this differential ISFET configuration include either using an ISFET and a reference field-effect transistor (REFET) (e.g. Errachid, et al., Sensors and Actuators B, vol. 60. (1999), pp. 43-48, Bergveld, et al., Sensors and Actuators B, vol. 18, (1989), pp. 309-327), or using two ISFETs with different pH sensitive layers (e.g. Wong and White, IEEE Trans. Electron Devices, vol. 36, (1989), pp. 479-487). However, both of these methods need post-processing of the commercially fabricated CMOS integrated circuit because a special pH insensitive layer must be deposited over the ISFET, or a different pH sensitive layer must be deposited on one of the ISFETs. This additional processing is specialized, and therefore negatively impacts the low cost and mass-producing capabilities of using a commercial CMOS process.

SUMMARY OF THE INVENTION

The invention may be embodied as a pH-change sensor. Such a sensor may have a first ion-sensitive transistor-operational-transconductance-amplifier (the "first IOTA") and a second ion-sensitive transistor-operational-transconductance-amplifier (the "second IOTA"). Each IOTA may have an ion-sensitive transistor, a load transistor, and an output. In each IOTA, the drain region of the ion-sensitive transistor may be connected to the drain region of the load transistor.

A differential sensor may be connected to the IOTAs, and an output from the differential sensor may indicate a voltage difference between the IOTA outputs. The output from the differential sensor may be used to provide an indication of a change in pH.

The IOTAs may respond differently to the same pH change. To accomplish this, the load transistor of the first IOTA may provide a drain-to-source resistance (the "first rds") that is different from the drain-to-source resistance provided by the second IOTA. The differing drain-to-source resistances may be provided by making the width of the channel region in the load transistor of the first IOTA different from the width of the channel region in the load transistor of the second IOTA.

The invention may be embodied as a method of indicating a change in the pH of a substance. In such a method, a pH-change sensor is provided. A first pH sensitive layer and the second pH sensitive layer of the sensor may be placed in contact with a substance. When the pH of the substance changes, a difference between an output of a first ion-sensitive transistor-operational-transconductance-amplifier and an output of a second ion-sensitive transistor-operational-transconductance-amplifier are detected. The difference between the outputs may be provided in order to indicate a change in the pH of the substance.

BRIEF DESCRIPTION OF THE DRAWINGS

For a fuller understanding of the nature and objects of the invention, reference should be made to the accompanying drawings and the subsequent description. Briefly, the drawings are.

FURTHER DESCRIPTION OF THE INVENTION

Figure 1:
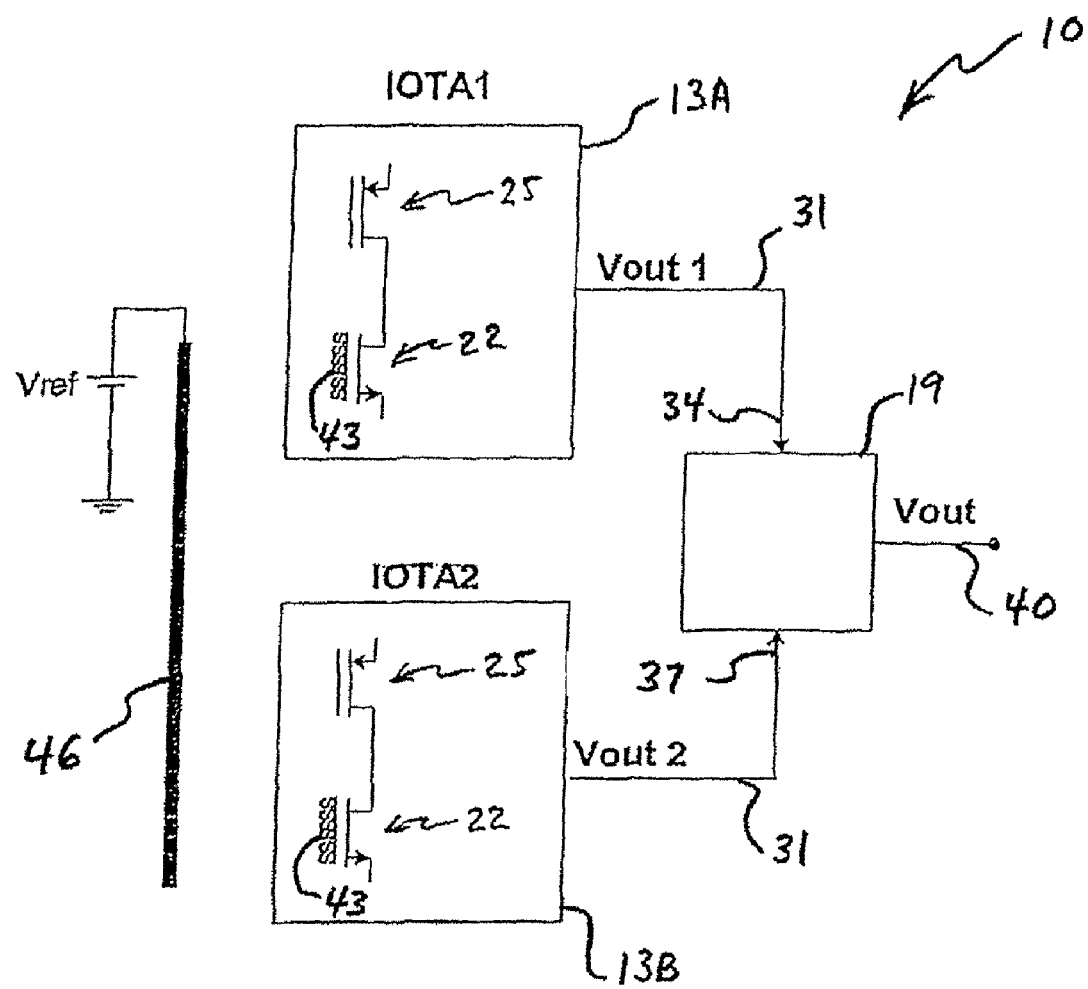
FIG. 1, which is a schematic diagram of a sensor according to the invention.

The invention may be embodied as a sensor 10 which can detect a change in pH. Such a pH-change sensor 10 may have a first ion-sensitive-transistor-operational-transconductance-amplifier (the "first IOTA") 13A, a second ion-sensitive-transistor-operational-transconductance-amplifier (the "second IOTA") 13B and a differential sensor 19. FIG. 1 depicts such a pH-change sensor 10.

Figure 2:
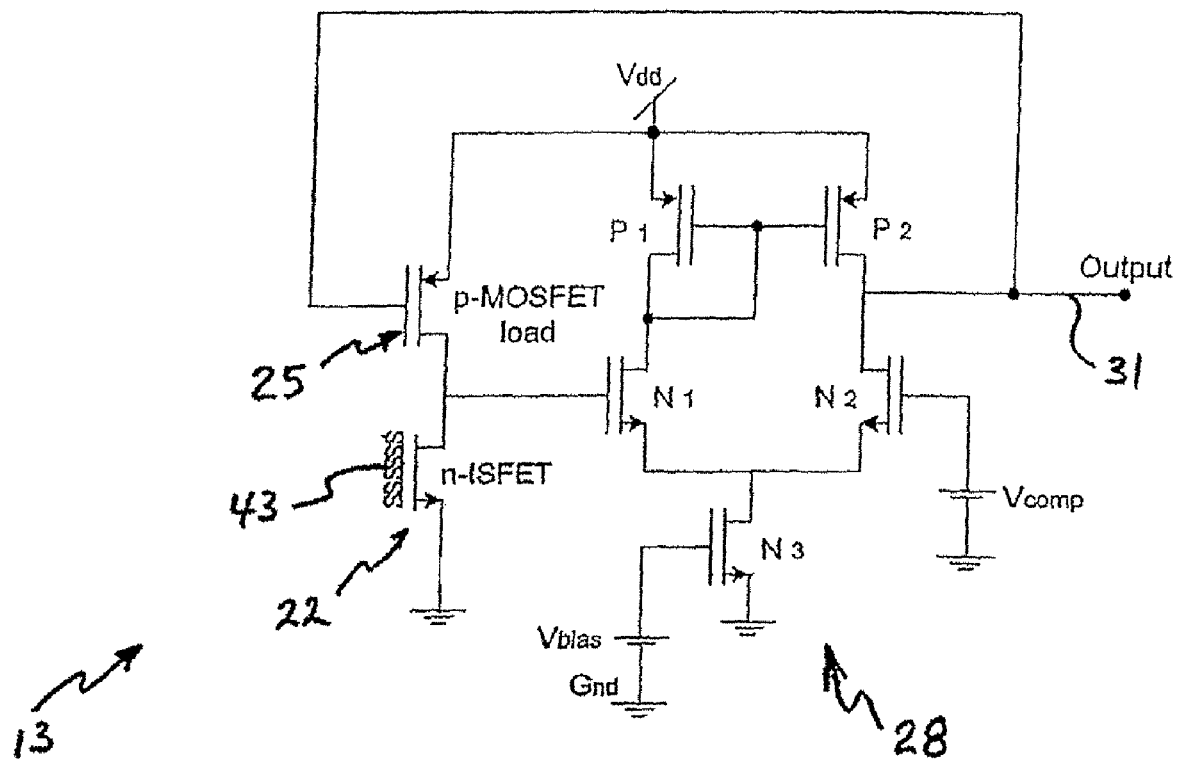
FIG. 2, which is a circuit diagram of an IOTA according to the invention.

FIG. 2 depicts an IOTA 13 according to the invention. In FIG. 2 there is shown an IOTA 13, which may have an ion-sensitive transistor (an "IST") 22, which is electrically connected to a load transistor (the "load transistor") 25. The IST 22 in FIG. 2 is an n-channel ion-sensitive field-effect transistor ("n-ISFET"). The IST 22 and the load transistor 25 may each be a field-effect transistor. The load transistor 25 may be a metal-oxide semiconductor field-effect transistor. The IST 22 may have a drain region, a source region and a channel region that electrically connects the drain and source regions of the IST 22. The load transistor 25 may have a source region, a drain region, and a channel region that electrically connects the source and drain regions of the load transistor 25. The drain region of the IST 22 may be electrically connected to the drain region of the load transistor 25.

The drains of the IST 22 and the load transistor 25 may be connected to an amplifier 28, which has an output 28 that may be considered the output for the IOTA 13. In FIG. 2, the amplifier 28 includes n-MOSFETs N1, N2 and N3 as well as p-MOSFETs P1 and P2. In FIG. 2, the IOTA output 31 is labeled "output" and in FIG. 1, the outputs 31 of the IOTAs 13A, 13B are labeled "Vout1" and "Vout2".

In this IOTA 13 design, a constant $V_{DS}$ (drain to source voltage) may be maintained across the IST 22 by changing the $I_D$ (drain current), which causes a change in the $V_{DS}$ (drain-to-source voltage) via the transconductance. This results in a change in the voltage of the drains. The drain voltage may be used as an input to the amplifier 28, compared with a fixed voltage ($V_{comp}$), and the difference may be amplified. The IOTA output 31 may be provided as the feedback signal to the load transistor 25, which again causes a change in the $I_D$ such that the $V_{DS}$ returns to its original value. Thus, a constant $V_{DS}$ may be maintained.

The ISTs 22 may employ a multilayer gate structure. The multilayer gate structure may have (1) an electrically-floating polysilicon layer, (2) two metal layers on top of the polysilicon layer, and (3) a silicon nitride ($Si_3N_4$) passivation layer on top of the metal layers. The design of the IST 22 shown in FIG. 2 is similar to the indirect gate-feedback circuit described by Morgenshtein, et al., in *Sensors and Actuators B*, vol. 97, (2004), pp. 122-131 and referred to as Complementary ISFET/MOSFET Pair ("CIMP").

The outputs 31 of the two IOTAs 13 may be in communication with the differential sensor 19. The differential sensor 19 may have a first input 34, a second input 37 and an output 40 (the "differential sensor output"). The differential sensor 19 may be a differential amplifier. The first input 34 of the differential sensor 19 may be in communication with the first output 31 of the first IOTA 13A. The second input 37 of the differential sensor 19 may be in communication with the second output 31 of the second IOTA 13B. The output 40 of the differential sensor 19 may be used to provide an indication of a voltage difference between the differential sensor's 19 first input 34 and the differential sensor's 19 second input 37.

In an embodiment of the pH-change sensor, the load transistor 25 of the first IOTA 13A (the "first load transistor 25") provides a drain-to-source resistance (the "first rds"), and the second load transistor 25 of the second IOTA 13B (the "second load transistor 25") provides a drain-to-source resistance (the "second rds"), and the first rds is different from the second rds. In this manner, the first IOTA 13A will react differently from the second IOTA 13B to a change in pH. Therefore, if the first and second IOTAs 13A, 13B are sensing the same change in pH, their outputs 31 will be different, and the differential sensor 19 will detect the difference and provide an indication of the differing outputs from the IOTAs 13A, 13B.

To provide the differing drain-to-source resistances, the channel region of the first load transistor 25 may have a width that is different from a width of the channel region of the second load transistor 25. Further, the lengths of the channel regions of the load transistors 25 may be made different in order to provide the differing drain-to-source resistances, but doing so might also require matching the lengths of the channel regions of the ISTs 22 so that the load transistors 25 and their respective ISTs 22 are able to operate properly together. Since it may be preferable to use similar ISTs 22 in both IOTAs 13A, 13B, the lengths of the channel regions of both load transistors 25 may need to be similar, and in that situation the differing drain-to-source resistances may be provided by making the widths of the channel regions of the load transistors 25 different.

The ISTs 22 may each be an ion-sensitive field-effect transistor. The IST 22 of the first IOTA 13A (the "first IST 22") and the IST 22 of the second IOTA 13B (the "second IST 22") may be substantially similar. For example, they may be similarly sensitive to pH. The ISTs 22 may each include a pH-sensitive layer 43. The pH-sensitive layer 43 may be silicon nitride ($Si_3N_4$), silicon oxide ($SiO_2$), aluminum oxide ($Al_2O_3$), Titanium Pent-oxide ($Ti_2O_5$) and Tin Oxide ($SnO_2$). The pH-sensitive layer 43 may be electrically connected to the gate of the IST 22.

Figure 3:
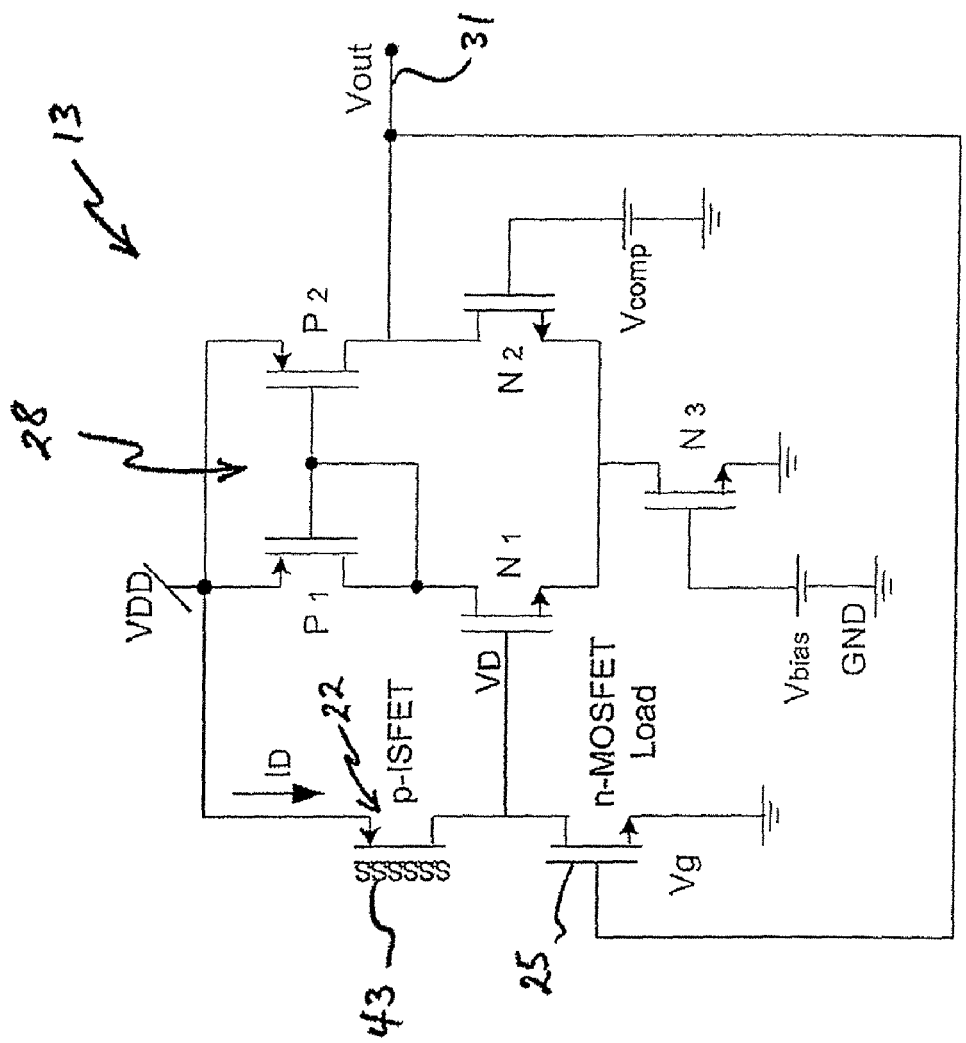
FIG. 3, which is a circuit diagram of another IOTA according to the invention.

In the embodiment depicted in FIG. 1 and FIG. 2, the ISTs 22 are n-channel transistors and the load transistors 25 are p-channel transistors. FIG. 3 depicts an embodiment of an IOTA 13 in which the IST 22 is a p-channel transistor and the load transistor 25 is an n-channel transistor.

A pH-change sensor 10 may use a gold wire as the reference electrode 46. The reference electrode 46 provides a source of electrons which may be detected by the ISTs 22. The reference electrode 46 may be placed on the same substrate as the IOTAs 13. Such a gold wire is typically available during integrated circuit packaging. This feature may enable the reference electrode 46 to be included during a commercial CMOS fabrication process without increasing the manufacturing costs.

The pH-change sensor 10 may be fabricated in a commercial CMOS process. Such a CMOS integrated circuit (IC) can be used as the pH-change sensor 10 without any specialized post-fabrication processing steps. As such, a pH-change sensor 10 according to the invention may have low power requirements and may be produced at low cost. The cost may be so low that such sensors 10 may be provided as disposable sensors 10.

Figure 4:
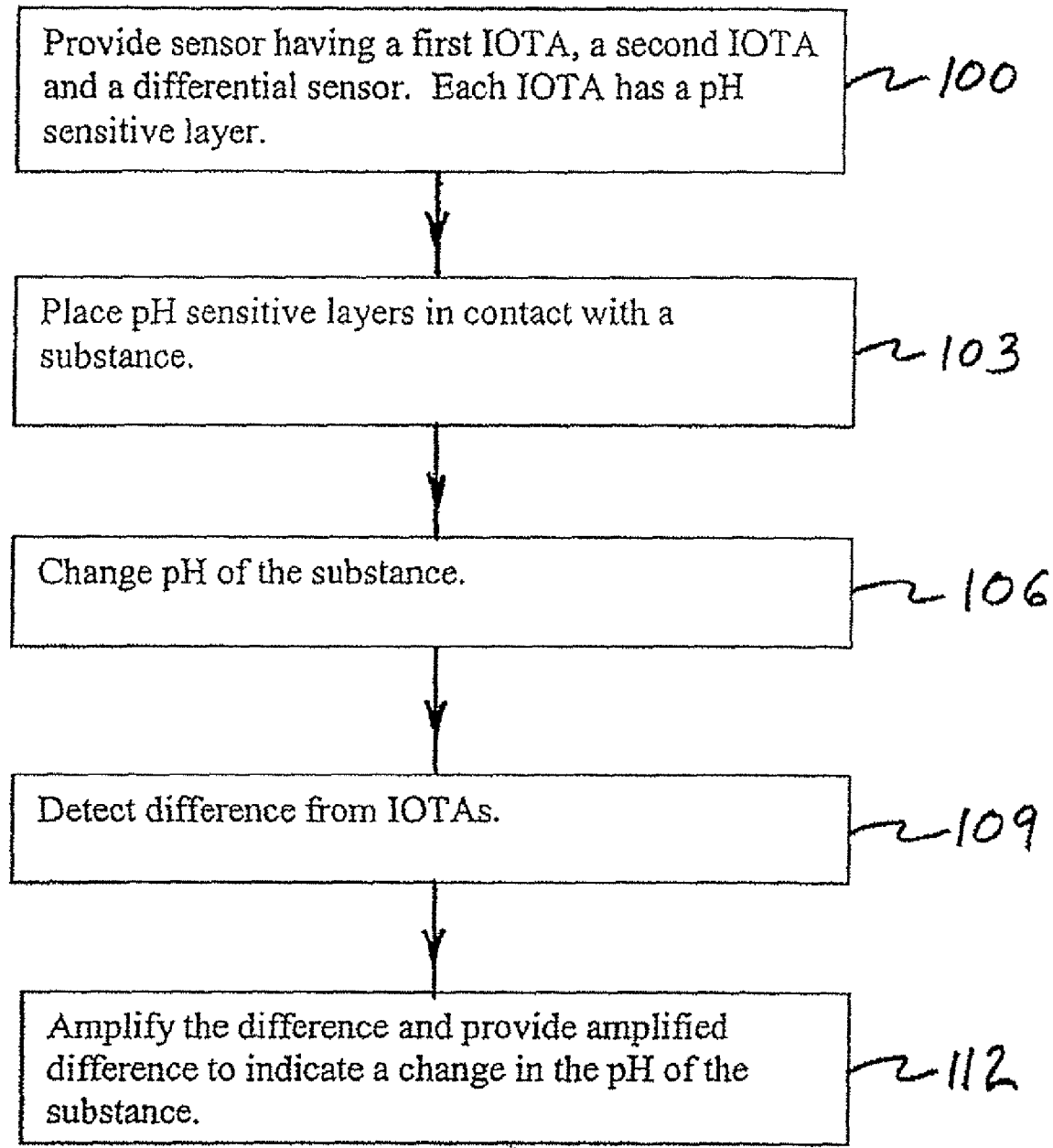
FIG. 4, which is a flow diagram of a method according to the invention.

The invention may be embodied as a method of indicating a change in pH. FIG. 4 is a flow diagram showing steps according to one such method. As an example of a method according to the invention, a sensor may be provided 100. In one such method, the sensor is calibrated using a substance having a known pH. A calibration system may be implemented on the same substrate as the IOTAs. Such a self-calibrating system should provide improved operation. After calibrating for the difference in the output DC levels due to the difference in the drain-to-source resistances of the load transistors, the result is a calibrated differential output from the pH-change sensor. The sensor may have:

(a) a first ion-sensitive-transistor-operational-transconductance-amplifier (the "first IOTA") having an ion-sensitive transistor (the "first IST") electrically connected to a load transistor (the "first load transistor"), and also having an output (the "first output), the first IST having a pH sensitive layer (the "first pH sensitive layer");

(b) a second ion-sensitive-transistor-operational-transconductance-amplifier (the "second IOTA") having an ion-sensitive transistor (the "second IST") electrically connected to a load transistor (the "second load transistor"), and also having an output (the "second output), the first IST having a pH sensitive layer (the "first pH sensitive layer"), wherein the first load transistor provides a drain-to-source resistance (the "first rds") in the first IOTA, and the second load transistor provides a drain-to-source resistance (the "second rds") in the second IOTA, and the first rds is different from the second rds, and (c) a differential sensor having a first input, a second input and an output (the "differential sensor output"), wherein the first input is in communication with the first output, wherein the second input is in communication with the second output, and wherein the differential sensor output may be used to provide an indication of a voltage difference between the first input and the second input.

The first pH sensitive layer and the second pH sensitive layer may be placed 103 in contact with a substance. For example, the substance may be the blood or saliva of a person on whom a medical procedure is being performed. When a pH of the substance changes 106, the first IOTA and the second IOTA will produce different outputs in response to the pH change. The differential sensor then detects 109 the difference between the IOTA outputs and may amplify 112 the difference to indicate a change in the pH of the substance.

Figure 5:
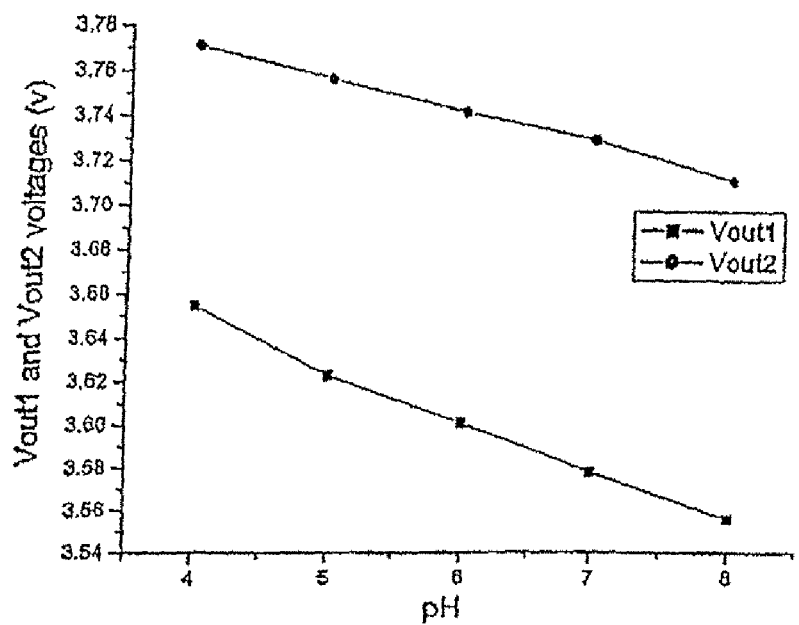
FIG. 5, which is a graph showing the pH of five solutions and the corresponding outputs of two IOTAs according to the invention.
Figure 6:
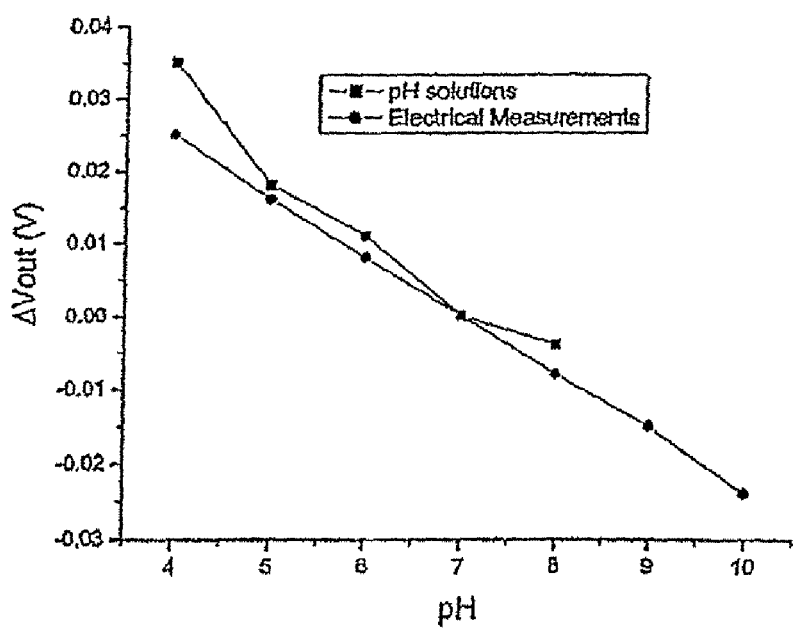
FIG. 6, which is a graph showing the differential response between the two IOTAs for different pH solutions and the comparative electrical measurement response.

To illustrate a sensor and method according to the invention, test results corresponding to a pH-change sensor 10 using five standard solutions of known pH at room temperature are shown in FIGS. 5 and 6. FIG. 5 shows pH measurements for the five solutions, and the corresponding outputs from the IOTAs 13. The first IOTA 13A had a sensitivity of 20 mV/pH, and the second IOTA 13B had a sensitivity of 12 mV/pH. FIG. 6 shows the calibrated differential output of the pH-change sensor 10. Such a sensor 10 consumed about 4 mW of power. The differential configuration created by using two IOTAs 13 allowed for the reduction, or almost elimination, of variations in the individual outputs 31 due to factors such as temperature and ambient light variations.

Using the invention, pH-change sensors 10 may be produced, which are improvements over the existing state of the art. Currently, it is possible to manufacture ISTs 22 in a commercial CMOS process, but none have been able to develop a pH-change sensor 10 without also engaging in specialized post-fabrication processing. An advantage of a pH-change sensor 10 according to the invention is the ability to manufacture the sensor in a commercial CMOS process without any specialized post-fabrication processing. The invention therefore provides for the manufacture of a low power, low cost disposable sensor 10 that can be more easily mass-produced. The invention also may provide the ability to develop sensors 10, signal processors and calibration circuits on a single integrated circuit. By providing for self-calibration and use of the gold bonding wire, it may be possible to realize improved performance, simplification of manufacturing and size reductions. Furthermore, the invention may allow for the development of a packaged sensor 10 with self-calibration and integration of the reference electrode 46, which may allow for such sensors 10 to be placed in a living organism.

In another embodiment of the invention, a xerogel 200 may be added to the pH-change sensor 10. The xerogel 200 may cover at least part of the pH-sensitive layer 43. A discussion of xerogels may be found at each of the following references: (1) C. J. Brinker and G. W. Scherer, Sol-Gel Science. New York: Academic, 1989, (2) B. C. Dave et al., "Sol-gel encapsulation methods for biosensors," Anal. Chem., vol. 66, pp. 1120A-1127A, 1994, (3) W. Jin and J. D. Brennan, "Properties and applications of proteins encapsulated within sol-gel derived materials," Anal. Chim. Acta, vol. 461, pp. 1-36, 2002, (4) R. A. Dunbar, J. D. Jordan and F. V. Bright, "Development of Chemical Sensing Platforms Based on a Sol-Gel-Derived Thin Film: Origin of Film Age vs. Performance Trade Offs," Analytical Chemistry, 1996, vol. 68, pp. 604-610, (5) C. M. Ingersoll and F. V. Bright, "Sol-Gel-Derived Materials as Chemical Sensing Platforms," *CHEMTECH*, 1997, vol. 27, pp. 26-31, (6) Y. Tang, E. C. Tehan, Z. Tao and F. V. Bright, "Sol-Gel-Derived Sensor Materials that Yield Linear Calibration Plots, High Sensitivity, and Long Term Stability," Analytical Chemistry, 2003, vol. 75, pp. 2407-2413. Xerogel based active recognition materials may provide a platform for the design of various sensing materials because xerogels 200 are relatively stable, electrically and chemically inert, and they may be tailored by sequestering various sensing materials within the xerogel 200 or by molecular imprinting strategies. Despite the above-mentioned advantages, there has not been a successful marriage of ISTs 22 with xerogels 200 based active recognition materials.

By combining an IST 22 with a xerogel 200 based active recognition material it may be possible to form very sensitive sensors. The term "XeroFET" is used herein to refer to an IST 22 that includes a xerogel 200 based active recognition material. For example, in an embodiment of a XeroFET 203, a glucose sensor may be produced. The invention is not limited to such a glucose sensor, and it is noted that other enzymes or indeed antibodies or molecular imprinting paradigms can be used. Such a glucose sensor may include an IST 22 fabricated in a commercial CMOS process with an integrated xerogel 200 layer encapsulating the enzyme glucose oxidase.

The IST 22 used in a XeroFET 203 could be based on n-channel or p-channel devices. An n-channel IST 22 is described herein because the performance of an n-channel IST 22 is expected to be better than a p-channel IST 22, in terms of stability, time response and pH-change sensitivity. The XeroFET 203 may be integrated as an input stage of the XeroFET operational transconductance amplifier ("XOTA") 206 on an integrated circuit, and may use silicon nitride as a pH sensitive layer 43, which may be applied in the manufacturing process as a surface passivation layer.

Figure 7:
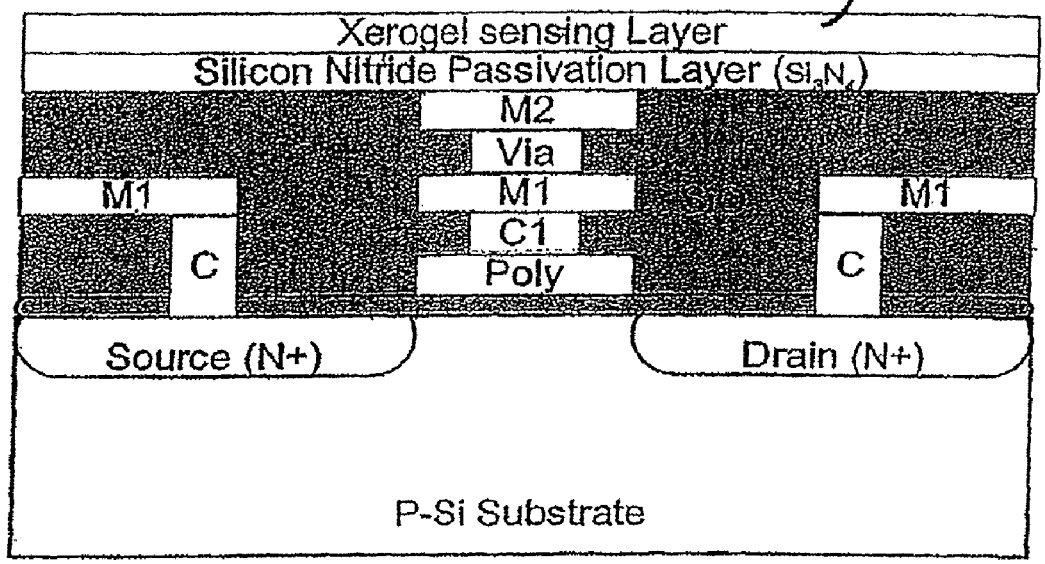
FIG. 7, which depicts a XeroFET according to the invention.

The structure of such a XeroFET 203 is shown in FIG. 7. In FIG. 7 there is shown a multilayer gate structure for a CMOS IST 22 which has an electrically-floating polysilicon layer ("Poly") with two metal layers ("M1" and "M2") on top of it and a silicon nitride ($Si_3N_4$) passivation layer (pH layer 43) on top of the metal layers ("M1" and "M2"). The xerogel 200 sensing layer may be deposited on the pH sensitive layer 43 in a post-fabrication processing step.

In an embodiment of the XeroFET 203, when the analyte of interest comes in contact with the sensing material embedded in the xerogel 200 layer, a reaction with the sensing material leads to a change in local pH which is detected by the IST 22. High selectivity may be achieved when the xerogel 200 sensing material reacts only with the analyte of interest. The sensing material in the xerogel 200 can be made selective to a variety of different analytes, creating the possibility of a wide range of sensors based on the same basic XeroFET 203 sensor platform.

The following descriptions include information about two types of devices: (1) XeroFET-based discrete selective sensors, and (2) XeroFET-based lab-on-a chip (microscale total analysis system). The descriptions of these devices are given as examples of how the invention might be implemented. The invention is not limited to these two devices.

Figure 8:
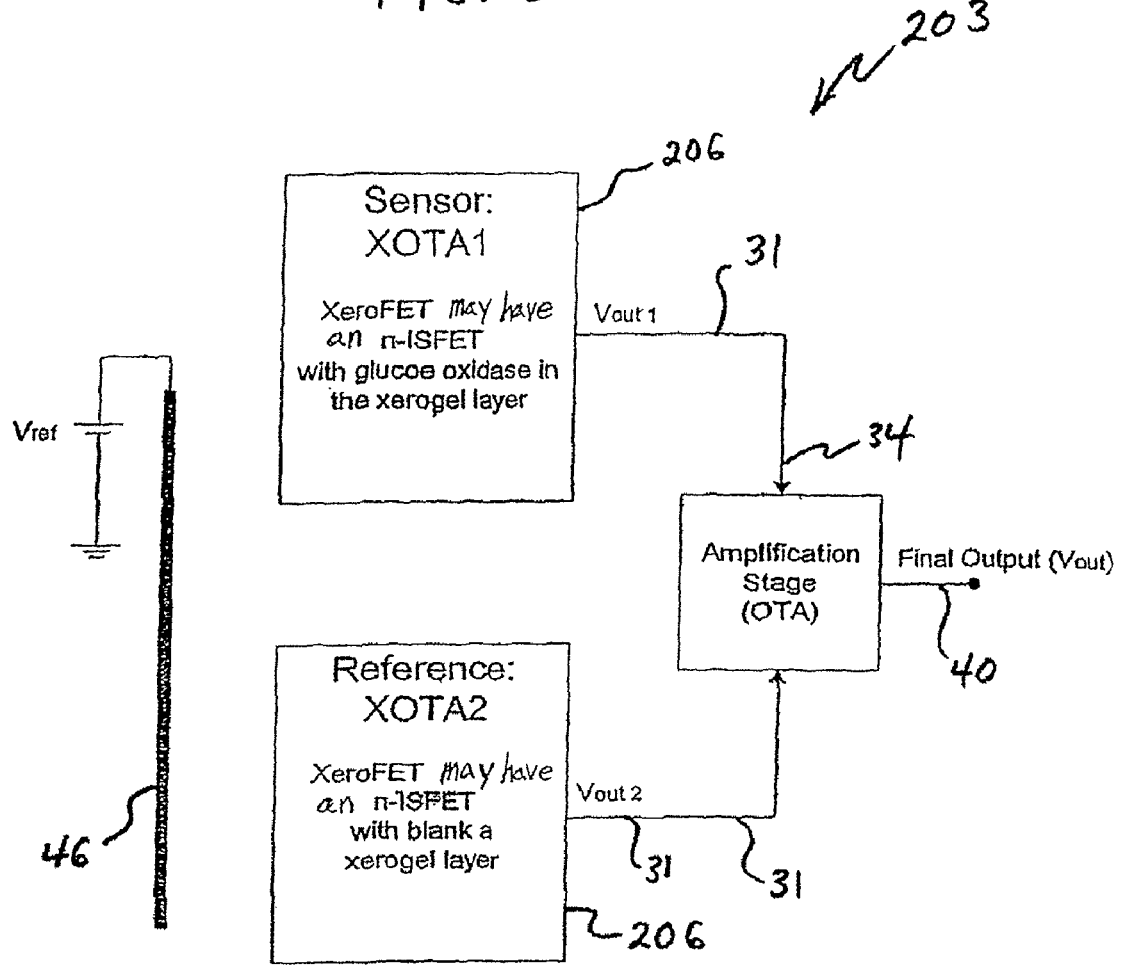
FIG. 8, which is a schematic diagram of a sensor according to the invention.

XeroFET-based Discrete Selective Sensors: In order to demonstrate the principle of a XeroFET-based discrete selective sensor, a description of a glucose sensor named "GlucoSen" is provided herein. The principles illustrated by GlucoSen may be used with other analytes to provide other types of sensors. A block diagram of a GlucoSen system is shown in FIG. 8. FIG. 8 shows a GlucoSen system with two XOTAs 206A, 206B in a differential configuration.

Figure 9:
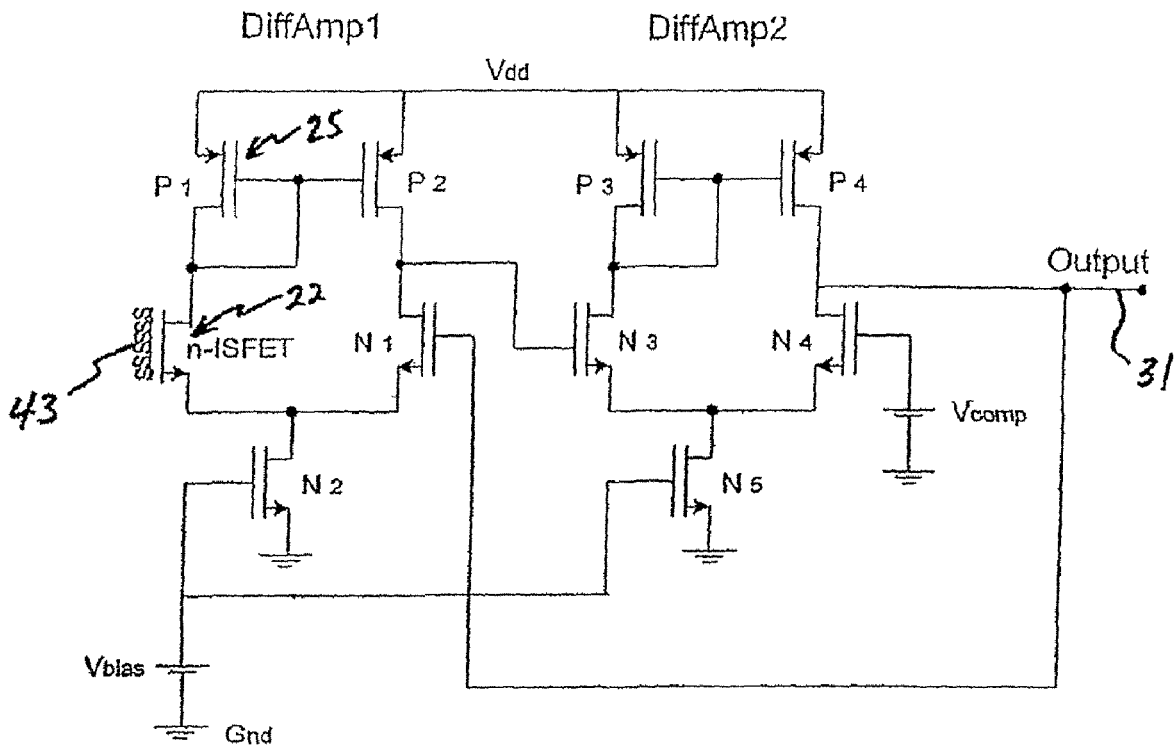
FIG. 9, which is a circuit diagram of a sensor according to the invention.

In the GlucoSen, the XOTAs 206 may be integrated as an input stage of the XeroFET sensor 203. A circuit diagram for an XOTA 206 is shown in FIG. 9. An XOTA 206 may have two operational transconductance amplifiers (DiffAmp1 and DiffAmp2) connected in a feedback loop. One of the XOTAs 206B may act as the reference and the other XOTA 206A may act as the sensor. For example, for XOTA1 206A the xerogel 200 layer may be a glucose oxidase-doped xerogel 200 layer which reacts in the presence of glucose to change the local pH (gluconic acid formation). XOTA2 206B may serve as a reference, and so the xerogel 200 layer of XOTA2 206B may be formed without the glucose oxidase, and hence may provide a constant output irrespective of the presence or the absence of the glucose.

The sensor system amplification stage may have an operational transconductance amplifier ("OTA") to amplify the difference between the output from the first XOTA ("XOTA1") 206A and the output from the second XOTA ("XOTA2") 206B so that the sensor can be made sensitive to a very small variation in the concentration of glucose. The OTA may amplify the difference between the outputs of the XOTAs 206 to provide an output proportional to the glucose concentration in the sample. The differential configuration created by using two XOTAs 206 may allow for the reduction, or almost elimination, of variations in the individual outputs due to factors such as temperature, ionic strength, adsorbates, and ambient light variations.

The xerogel 200 may be a porous layer having a thickness that does not significantly alter the sensing properties of the sensor. The thickness of the porous layer may be 1 μm to 1 mm thick, but typically, the thickness will be 1 μm to 2 μm. The xerogel 200 layer may be applied by a pin-pointed process, or spin/dip coating process, and hence the process can be automated to mass-produce the sensor.

Figure 10:
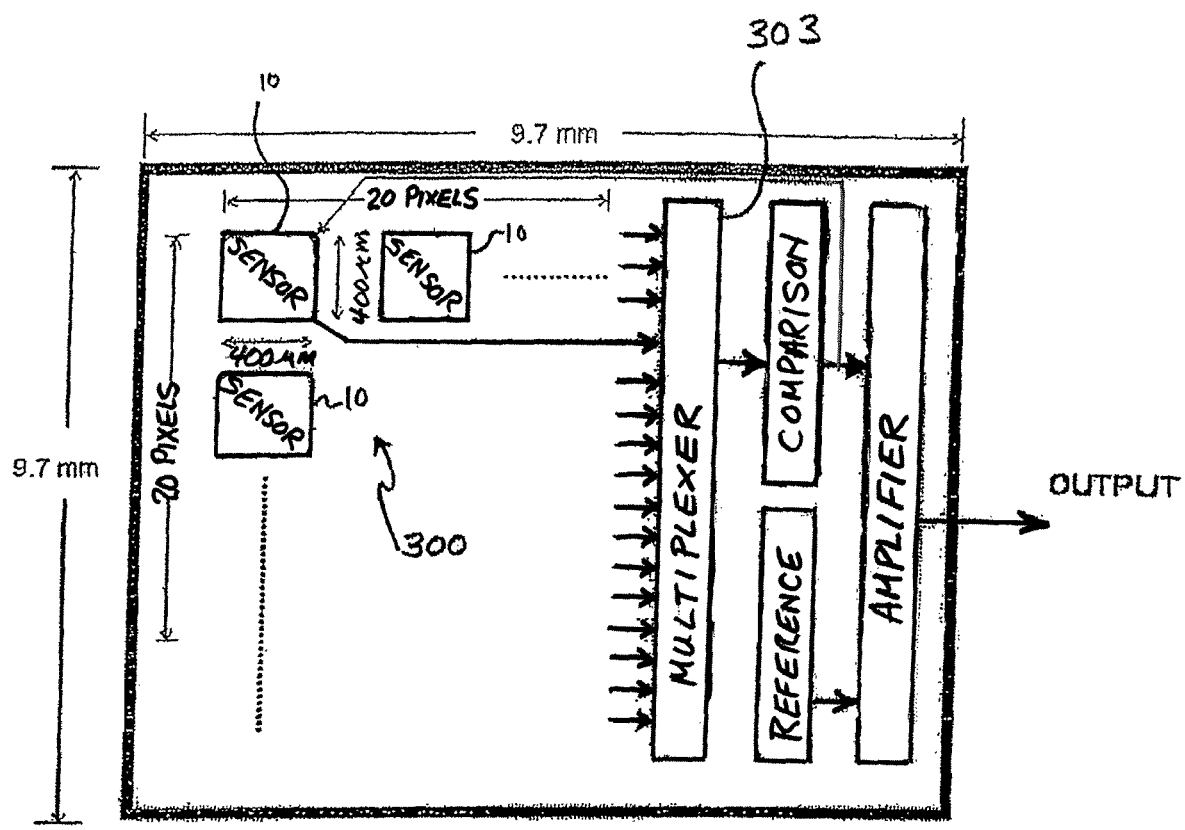
FIG. 10, which is a block diagram of a sensor according to the invention.

XeroFET-based lab-on-a chip: The invention may be embodied in a system that is sometimes referred to herein as a lab-on-a chip. FIG. 10 depicts such a system. The system may have several copies of the DiffAmp1 of the XOTA arranged as an array 300 on a single CMOS integrated circuit. In addition, the XeroFET in each copy of the DiffAmp1 of the XOTA may be made selective to a particular analyte, and thus the system may be sensitive to many different analytes. Alternatively, the array of copies, or some portion of the array, may be made selective to the same analyte, but to different concentrations of the analyte. Strategies for doing this are described in the following documents: (1) Z. Tao, E. C. Tehan, R. M. Bukowski, Y. Tang, E. L. Shughart, W. G. Holthoff, A. N. Cartwright, A. H. Titus, and F. V. Bright, "Templated xerogels as platforms for biomolecule-less biomolecule sensors," Analytica Chimica Acta, vol. 564, pp. 59-65, 2006, (2) Y. Tang, Z. Tao, R. M. Bukowski, E. C. Tehan, S. Karri, A. H. Titusb and F. V. Bright, "Tailored Xerogel-Based Sensor Arrays and Artificial Neural Networks Yield Improved Accuracy and Precision," Analyst, vol. 131, no. 10, pp. 1129-1136, 2006, (3) A. N. Watkins, B. R. Wenner, J. D. Jordan, W. Y. Xu, J. N. Demas and F. V. Bright, Appl. Spectrosc., 1998, 52, 750-754, (4) X. Chen, Z. M. Zhong, Z. Li, Y. Q. Jiang, X. R. Wang and K. Y. Wong, Sens. Actuators, B: Chem., 2002, 87, 233-238, (5) Y. Tang, E. C. Tehan, Z. Tao and F. V. Bright, Anal. Chem., 2003, 75, 2407-2413, (6) Y. E. L. Koo, Y. Cao, R. Kopelman, S. M. Koo, M. Brasuel and M. A. Philbert, Anal. Chem., 2004, 76, 2498-2505, (7) R. M. Bukowski, R. Ciriminna, M. Pagliaro and F. V. Bright, Anal. Chem., 2005, 77, 2670-2672, (8) E. J. Cho, Z. Tao, E. C. Tehan and F. V. Bright, "Pin-Printed Biosensor Arrays for Simultaneous Detection of Glucose and O 2," Analytical Chemistry, 2002, vol. 74, pp. 6177-6184. Such a device may be used for imaging applications and for studying entire cells or particular parts of a cell/organ system.

The XeroFET-based lab-on-a chip system may have a multiplexer system 303, which selects an IOTA 13A (or XOTA 206A) having a pH sensitive layer 43 in the array 300 at any instant of time and connects that IOTA 13A (or XOTA 206A) to the "comparison stage" 306. The "reference stage" may have a reference IOTA 13B (or XOTA 206B), which measures the ambient pH irrespective of the presence or the absence of the analyte. The "amplifier stage" may be the differential sensor 19, which may have an OTA to provide the ability to detect small variations in the outputs 31 in order to detect small variations in the pH or concentration of the analyte, as the case may be.

There are existing applications of ISTs 22 with integrated recognition materials in sensors, such as sensors for glucose, urea, sucrose and lactose as well as biomarkers and proteins.

However, there is no single sensor platform which is useful in detecting a variety of analytes, consumes relatively little power, is low in cost and that can be easily mass produced. Moreover, in the case of the lab-on-a chip, there are MEMS based products which are expensive to produce but have higher resolution in terms of the number of analytes which can be detected simultaneously. XeroFET-based sensors may provide a low cost, low power platform for developing a wide range of sensors, such as biochemical sensors, that can easily be mass-produced.

U.S. provisional patent application No. 60/725,777 discloses additional details about the invention and additional embodiments of the invention. The disclosure of that patent application is incorporated by this reference.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A pH-change sensor, comprising:
    a first IST-operational-transconductance-amplifier (the "first IOTA") having:
        (a) an output (the "first IOTA output"),
        (b) an ion-sensitive transistor (the "first IST") having a drain region, and
        (c) a load transistor (the "first load transistor") having a source region, a drain region, and a channel region, the channel region electrically connecting the source region and the drain region,
        wherein the drain region of the first IST is electrically connected to the drain region of the first load transistor;
    a second IST-operational-transconductance-amplifier (the "second IOTA") having:
        (a) an output (the "second IOTA output"),
        (b) an ion-sensitive transistor (the "second IST") having a drain region, and
        (c) a load transistor (the "second load transistor") having a source region, a drain region and a channel region, the channel region electrically connecting the source region and the drain region,
        wherein the drain region of the second IST is electrically connected to the drain region of the second load transistor;
    a differential sensor having:
        (a) a first input connected to the first IOTA output,
        (b) a second input connected to the second IOTA output, and
        (c) an output (the "differential sensor output"), wherein the differential sensor output may be used to provide an indication of a voltage difference between the first input and the second input;
    wherein the first load transistor provides a drain-to-source resistance (the "first rds"), and the second load transistor provides a drain-to-source resistance (the "second rds"), and the first rds is different from the second rds.

2. The sensor of claim 1, wherein the first IST is an ion-sensitive field-effect transistor.

3. The sensor of claim 1, wherein the first IST is an n-channel transistor.

4. The sensor of claim 3, wherein the first load transistor is a p-channel transistor.

5. The sensor of claim 1, wherein the first IST is a p-channel transistor.

6. The sensor of claim 5, wherein the first load transistor is an n-channel transistor.

7. The sensor of claim 1, wherein the first load transistor is a field-effect transistor.

8. The sensor of claim 7, wherein the first load transistor is a metal-oxide semiconductor field-effect transistor.

9. The sensor of claim 1, wherein the channel region of the first load transistor has a width that is different from a width of the channel region of the second load transistor.

10. The sensor of claim 9, wherein the channel region of the first load transistor has a length that is substantially similar to a length of the channel region of the second load transistor.

11. The sensor of claim 1, wherein the first IST and the second IST are substantially similar.

12. The sensor of claim 1, wherein the first IST and the second IST are substantially similarly sensitive to pH.

13. The sensor of claim 1, wherein the differential sensor is a differential amplifier.

14. The sensor of claim 1, wherein the first IST includes a pH-sensitive layer comprised of a compound selected from the group of silicon nitride (Si3N4), silicon oxide (SiO2), aluminum oxide (Al2O3), Titanium Pent-oxide (Ti2O5) and Tin Oxide (Sn02).

15. The sensor of claim 1, wherein the first IST has a pH sensitive layer that is electrically connected to a gate of the first IST.

16. The sensor of claim 15, wherein the first IST further comprises a xerogel at least partially covering the pH-sensitive layer.

17. A pH-change sensor, comprising:
    a first ion-sensitive-transistor-operational-transconductance-amplifier (the "first IOTA") having an ion-sensitive transistor (the "first IST") electrically connected to a load transistor (the "first load transistor"), and also having an output (the "first output");
    a second ion-sensitive-transistor-operational-transconductance-amplifier (the "second IOTA") having an ion-sensitive transistor (the "second IST") electrically connected to a load transistor (the "second load transistor"), and also having an output (the "second output");
    a differential sensor having a first input, a second input and an output (the "differential sensor output"), wherein the first input is in communication with the first output, wherein the second input is in communication with the second output, wherein the differential sensor output may be used to provide an indication of a voltage difference between the first input and the second input;
    wherein the first load transistor provides a drain-to-source resistance (the "first rds"), and the second load transistor provides a drain-to-source resistance (the "second rds"), and the first rds is different from the second rds;
    wherein the first IST and the second IST are substantially similarly sensitive to pH.

18. The sensor of claim 17, wherein the first IST is an ion-sensitive field-effect transistor.

19. The sensor of claim 17, wherein the first IST and the second IST are substantially similar.

20. The sensor of claim 17, wherein the differential sensor is a differential amplifier.

21. The sensor of claim 17, wherein the first IST includes a pH-sensitive layer comprised of a compound selected from the group of silicon nitride (Si3N4), silicon oxide (SiO2), aluminum oxide (Al2O3), Titanium Pent-oxide (Ti2O5) and Tin Oxide (Sn02).

22. The sensor of claim 21, wherein the first IST has a pH-sensitive layer that is electrically connected to the gate of the first IST.

23. The sensor of claim 22, wherein the first IST further comprises a xerogel at least partially covering the pH-sensitive layer.

24. A method of indicating a change in pH, comprising:
providing a sensor having:
- (a) a first ion-sensitive-transistor-operational-transconductance-amplifier (the "first IOTA") having an ion-sensitive transistor (the "first IST") electrically connected to a load transistor (the "first load transistor"), and also having an output (the "first output), the first IST having a pH sensitive layer (the "first pH sensitive layer");
- (b) a second ion-sensitive-transistor-operational-transconductance-amplifier (the "second IOTA") having an ion-sensitive transistor (the "second IST") electrically connected to a load transistor (the "second load transistor"), and also having an output (the "second output), the second IST having a pH sensitive layer (the "second pH sensitive layer"), wherein the first load transistor provides a drain-to-source resistance (the "first rds") in the first IOTA, and the second load transistor provides a drain-to-source resistance (the "second rds") in the second IOTA, and the first rds is different from the second rds, and
- (c) a differential sensor having a first input, a second input and an output (the "differential sensor output"), wherein the first input is in communication with the first output, wherein the second input is in communication with the second output, and wherein the differential sensor output may be used to provide an indication of a voltage difference between the first input and the second input;

placing the first pH sensitive layer and the second pH sensitive layer in contact with a substance;

changing a pH of the substance;

detecting a difference between an output of the first IOTA and an output of the second IOTA, and providing the difference to indicate a change in the pH of the substance.

* * * * *